(12) United States Patent
Estévez Company et al.

(10) Patent No.: US 7,595,425 B2
(45) Date of Patent: Sep. 29, 2009

(54) FRIEDEL-CRAFTS ACYLATION PROCESS IN IONIC LIQUIDS

(75) Inventors: Carles Estévez Company, Mollet del Vallés (ES); Lidia Gallä Prats, Mollet del Vallés (ES); Josep Castells Boliart, Mollet del Vallés (ES)

(73) Assignee: Institut Universitari de Ciencia I Tecnologia, Mollet del Valles (ES)

( * ) Notice: Subject to any disclaimer, the term of this patent is extended or adjusted under 35 U.S.C. 154(b) by 306 days.

(21) Appl. No.: 10/586,786

(22) PCT Filed: Jan. 20, 2005

(86) PCT No.: PCT/ES2005/000024

§ 371 (c)(1),
(2), (4) Date: Jul. 21, 2006

(87) PCT Pub. No.: WO2005/070861

PCT Pub. Date: Apr. 8, 2005

(65) Prior Publication Data

US 2008/0306307 A1    Dec. 11, 2008

(30) Foreign Application Priority Data

Jan. 21, 2004    (ES) ................ 200400191

(51) Int. Cl.
C07C 45/46    (2006.01)
(52) U.S. Cl. ................... 568/309; 568/314
(58) Field of Classification Search ............ 568/322
See application file for complete search history.

(56) References Cited

U.S. PATENT DOCUMENTS

| 6,969,693 | B2 * | 11/2005 | Sauvage et al. | 502/159 |
| 7,119,235 | B2 * | 10/2006 | Hardacre et al. | 568/322 |
| 2002/0169071 | A1 * | 11/2002 | Sauvage et al. | 502/150 |
| 2004/0171895 | A1 * | 9/2004 | Earle et al. | 570/143 |
| 2005/0054694 | A1 * | 3/2005 | Seddon et al. | 514/362 |

FOREIGN PATENT DOCUMENTS

WO    WO 02/072519 A2    9/2002
WO    WO 03/028882 A1    4/2003

OTHER PUBLICATIONS

S. Gmouh et al., "Activation of Bismuth (III) Derivatives in Ionic Liquids: Novel and Recyclable Catalytic Systems for Friedel-Crafts Acylation of Aromatic Compounds", Org. Lett., 2003, pp. 2219-2222, vol. 5, No. 13, American Chemical Society, USA.
V.D. Sarca et al., "Triflic acid-promoted transacylation and deacylation reactions in ionic liquid solvents", Green Chemistry, 2004, pp. 245-248, vol. 6, No. 5, The Royal Society of Chemistry, United Kingdom.
J. Ross et al., "Friedel-Crafts acylation reactions using metal triflates in ionic liquids", Green Chemistry, 2002, pp. 129-133, vol. 4, No. 2, The Royal Society of Chemistry, United Kingdom.
T. Welton, "Room-Temperature Ionic Liquids. Solvents for Synthesis and Catalysis." Chem. Rev., 1999, pp. 2071-2083, vol. 99, No. 8, American Chemical Society, USA.
R. Sheldon, "Catalytic reactions in ionic liquids", Chem. Commun., 2001, pp. 2399-2407, vol. 23, The Royal Society of Chemistry, United Kingdom.
Institut Univ. de Ciencia Y Tecnologia, Estevez Company, Carles y otros, PCT Informe de Busqueda Internactional, 2005, Spain.
PCT (Elena Davila Muro), Opinion Escrita de la Administraction Encargada de la Busqueda Internacional, Apr. 29, 2005, Oficina Espanola de Patentes y Marcas, Spain.

* cited by examiner

*Primary Examiner*—Sikarl A Witherspoon
(74) *Attorney, Agent, or Firm*—Peter B. Scull; K Kalan; Berenbaum Weinshienk PC

(57) ABSTRACT

A preparation process of aromatic ketones by a Friedel-Crafts acylation reaction in an ionic liquid of formula (I), in the absence of any other catalyst and/or solvent. In formula (I), $[Q]^+$ is selected from substituted-imidazolium cations, substituted-pyridinium cations, ammonium cations, and phosponium cations. It allows to carry out Friedel-Crafts acylations with good yields and high selectivity in para position of the Friedel-Crafts aromatic substrate without using chlorine-containing solvents and conventional Friedel-Crafts catalysts. It is industrially useful because provides a "Green Chemistry" technology for carrying out Friedel-Crafts acylations of general aplicability.

$$[Q]^+[CF_3SO_3]^- \qquad (I)$$

16 Claims, No Drawings

FRIEDEL-CRAFTS ACYLATION PROCESS IN IONIC LIQUIDS

BACKGROUND ART

Friedel-Crafts acylations are a well-known class of reactions with a great industrial importance for the preparation of aryl ketones by acylation of arenes (cf. e.g. the textbook M. B. Smith and J. March, "March's Advanced Organic Chemistry" 2001, 5$^{th}$ edition, Ed. John Wiley & Sons, pp. 712-716, and reviews cited therein). Reagents used are not only acyl halides but also carboxylic acids, esters, anhydrides, and ketenes (cf. e.g. R. C. Larock, "Comprehensive Organic Transformations" 1989, VCH: NY, p. 315; and B. C. Ranu et al., *J. Org. Chem.* 1996, vol. 61, p. 9546). A general reaction scheme could be:

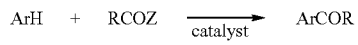

where ArH represents a Friedel-Crafts aromatic substrate and RCOZ represents a Friedel-Crafts acylating agent selected from those mentioned above.

Friedel-Crafts acylations are generally performed using a Lewis acid catalyst, commonly $AlCl_3$. However, there are several drawbacks associated with this type of reactions. Friedel-Crafts acylations are not truly catalytic reactions, as they actually consume one molar equivalent of $AlCl_3$ per mole of reactant. The net result is massive usage of $AlCl_3$ and problems associated with disposal of salts and oxide by-products. In fact, the isolation of the product typically is carried out by quenching the reaction mixture with water. The hydrolysis process generates a large amount of aqueous solutions and suspensions containing aluminum salts, which requires additional treatment steps for eventual disposal of those solutions and suspensions, and which significantly increases the cost of the process.

Another drawback derived from the industrial application of Friedel-Crafts reactions relates to the solvents used. Common solvents for the reaction include chlorine-containing solvents such as methylene chloride or 1,2-dichloroethylene, and volatile hydrocarbon solvents.

In today's society the introduction of cleaner technologies in industry (the so-called "Green Chemistry") has become a major concern. Thus, the search for alternatives to environmentally damaging solvents has become a topic of highest priority. In the past few years, ionic liquids have received an upsurge of interest as green solvents, mainly as replacements for conventional media in chemical processes.

Ionic liquids are organic salts with melting points under 300° C., often under room temperature. The most common cations in ionic liquids are imidazolium and pyridinium derivatives, although phosphonium and tetraalkylammonium derivatives often can also be used. Some suitable anions for ionic liquids are $Cl^-$, $Br^-$, $I^-$, $PF_6^-$, $CF_3CO_2^-$, $CH_3CO_2^-$, $CF_3CO_2^-$, $SO_4^{2-}$, $NO_3^-$, and $AlCl_4^-$.

Ionic liquids have several properties that make them suitable as potential solvents for synthesis. They are liquids in a wide temperature range. They do not have measurable vapor pressure, therefore reactions can be carried out in closed reactors without any vapor release to the atmosphere. They show very good dissolution properties for most organic and inorganic compounds. They act as Brönsted acids, Lewis acids and/or superacids. Usually they have a high thermal stability up to 200° C. They are non-flammable, not expensive and easy to prepare.

The use of some ionic liquids in Friedel-Crafts acylations carried out with conventional Friedel-Crafts catalyst is known in the art and some patent applications on the subject have been published. Patent application WO 99/19288 describes a somewhat special Friedel-Crafts acylation, carried out in the presence of a complex catalytic ionic liquid system consisting of a Lewis acid (e.g. $FeCl_3$) and a compound of formula QCl, Q being an organic cation.

Several alternative materials to Lewis acids have been proposed as catalysts for conventional Friedel-Crafts acylations, including zeolites, superacids, the lithium perchlorate/lanthanum triflate system, etc. But these catalysts are generally effective only under restrictive circumstances (cf. e.g. A. Kawada et al., *Chem. Commun.* 1996, p. 183; A. Kawada et al., *Synlett,* 1994, p. 545; and R. Sreekumar et al., *Synth. Commun.* 1997, vol. 27, p. 777). Zeolites have also been proposed as catalyst for Friedel-Crafts acylations in ionic liquids (cf. WO 03/028882). Thus, from what is known in the art it is derived that the provision of a reaction system for Friedel-Crafts acylations which use neither toxic solvents nor conventional Friedel-Crafts catalysts would be of great interest in industry.

SUMMARY OF THE INVENTION

According to an aspect of the present invention, there is provided a preparation process of aromatic ketones by a Friedel-Crafts acylation reaction in an ionic liquid, between a Friedel-Crafts aromatic substrate and a Friedel-Crafts acylating agent, characterized in that the ionic liquid has the formula (I) and it is used in the absence of any other catalyst and/or solvent; where $[Q]^+$ is selected from the group consisting of substituted-imidazolium cations, substituted-pyridinium cations, ammonium cations, and phosponium cations. Preferably, $[Q]^+$ is a substituted imidazolium cation.

By Friedel-Crafts aromatic substrate and Friedel-Crafts aromatic acylating agent it is respectively meant any substrate and any reagent which are able to give an aromatic ketone by the acyl-de-hydrogenation classically known as Friedel-Crafts acylation, a textbook reaction that is assumed to occurs via an aromatic electrophilic substitution and that usually needs a Lewis acid catalyst (see general references cited above).

Preferred ionic liquids of formula (I) are 1-ethyl-3-methylimidazolium trifluoromethanesulfonate, 1,3-diethylimidazolium trifluoromethanesulfonate, and 1,3-dimethylimidazolium trifluoromethanesulfonate. The most preferred ionic liquid is 1-ethyl-3-methylimidazolium trifluoromethanesulfonate.

In performing the Friedel-Crafts acylation, an aromatic substrate and an acylating agent are reacted together in the presence of the above-mentioned ionic liquids under suitable conditions to produce an aromatic ketone. Apparently, the ionic liquid simultaneously functions both as solvent and as catalyst.

The reaction is useful with many types of substrates. Preferably, the Friedel-Crafts acylation agent is selected from carboxylic acid halides, carboxylic acid anhydrides, carboxylic acid esters and carboxylic acids. More preferably, the Friedel-Crafts acylating agent is a carboxylic acid anhydride.

In a preferred embodiment of the present invention the Friedel-Crafts acylating agent is acetic acid anhydride, propionoic acid anhydride, butanoic acid anhydride, isobutanoic acid anhydride, pentanoic acid anhydride, benzoic acid anhydride, chloroacetic acid anhydride, acetyl chloride, propanoyl chloride, butanoyl chloride, benzoyl chloride, or chloroacetyl chloride.

Friedel-Crafts aromatic substrate is selected from aromatic benzenoid compounds, aromatic benzenoid-fused compounds, and heteroaromatic compounds resulting from substitution of CH groups by N atoms in the previous ones; all these substrates being optionally substituted by substituents which are stable under Friedel-Crafts reaction conditions, or which have been suitably protected to be stable, according to the general common knowledge of a person skilled in the art (cf. eg. T. W. Greene and P. G. M. Wuts, "Protective Groups in Organic Synthesis", $3^{th}$ edition 1999, Ed. John Wiley & Sons). Compounds containing ortho-para directing groups, including alkyl, hydroxy, alcoxy, halogen, and acetamido groups, are easily acylated and give mainly or exclusively the para products. Preferably, the Friedel-Crafts aromatic substrate is benzene, toluene or anisole. More preferably, the aromatic substrate is anisole.

In a particular embodiment, the Friedel-Crafts acylating agent is attached to the Friedel-Crafts aromatic substrate, being the carbonyl group of the Friedel-Crafts acylating agent separated from the Friedel-Crafts aromatic substrate by a aliphatic chain from 2 to 4 carbon atoms, so an intramolecular ring closure is done, yielding a (5-7)-membered ring.

Appropriate reaction conditions can be readily determined by the skilled person. In a preferred embodiment of the present invention, the reaction is carried out between room temperature and 150° C. In a more preferred embodiment, the reaction is carried out between 70 and 100° C.

Unless otherwise indicated, the terms used herein have the meanings indicated below. The term "Friedel-Crafts acylating agent" include compounds of the general formulae $R^1COX$, $R^1COOCOR^2$, $R^1COOH$, and $R^1COOR^2$; where X is a leaving group selected from Cl and Br; $R^1$ and $R^2$ are radicals, same or different, selected from the group consisting of H, $(C_1-C_{40})$-alkyl, $(C_1-C_{40})$-alkenyl, $(C_1-C_{40})$-alkynyl, or any of those groups substituted with $(C_1-C_6)$-alkyl, $(C_1-C_6)$-alcoxy, CN, OH or $NO_2$; $R^1$ and $R^2$ can also be selected from β-naphtyl, phenyl, Ph-$(CH_2)_n$- with n=1-3, aliphatic heterocycles and aromatic heterocycles, and a radical derived from those through a mono- or a di-substitution on their rings, the substituents being a radical independently selected from the group consisting of halogen, $(C_1-C_4)$-alkyl, $(C_1-C_4)$-alcoxy, CN, OH or $NO_2$.

The term "aromatic benzenoid compounds" is used to refer a single aromatic ring or multiple aromatic ring(s), or one or more aromatic rings coupled to one or more non-aromatic rings, linked by a group such as methylene or ethylene moiety. The common linking group may also be a carbonyl as in benzophenone. They may be substituted by one or more substituents which are stable under Friedel-Crafts reaction conditions, or which have been suitably protected to be stable.

The term "aromatic benzenoid-fused compounds" refers to multiple aromatic ring(s) which are fused together. They also may be substituted by one or more substituents which are stable under Friedel-Crafts reaction conditions, or which have been suitably protected to be stable.

The term "heteroaromatic compounds" refers to aromatic rings in which one or more carbon atoms of the aromatic ring(s) are substituted by N. They are structures that may be a single aromatic ring, multiple aromatic ring(s), or one or more aromatic rings coupled to one or more non-aromatic rings. In structures having multiple rings, the rings can be fused together, linked covalently, or linked to a common group such as methylene or ethylene moiety. The heteroaromatic compound may be substituted by one or more substituents which are stable under Friedel-Crafts reaction conditions, or which have been suitably protected to be stable. As used herein, suitable heteroaromatic compounds are for example pyridine, indole, phtalimide, purine, pirimidine, etc.

Substituents which are stable under Friedel-Crafts reaction conditions, or which have been suitably protected to be stable include for example alkyl, hydroxy, alcoxy, halogen, and acetamido groups.

The present invention allows to carry out Friedel-Crafts acylations with good yields and high selectivity in para position of the Friedel-Crafts aromatic substrate. It is advantageous with regard to conventional Friedel-Crafts acylation reactions, since chlorine-containing solvents and conventional Friedel-Crafts catalysts are not used. Besides, aqueous work-up is not required to isolate the product of the reaction. Thus, the product can be easily separated from the ionic liquid by a physical process such as for example by solvent extraction with an inert solvent. Furthermore, the ionic liquid can be reused for further reactions once the previous products/reactants have been removed.

Throughout the description and claims the word "comprise" and variations of the word, are not intended to exclude other technical features, additives, components, or steps. The abstract of this application is incorporated herein as reference. Additional objects, advantages and features of the invention will become apparent to those skilled in the art upon examination of the description or may be learned by practice of the invention. The following examples are provided by way of illustration, and they are not intended to be limiting of the present invention.

EXAMPLES

Example 1

Preparation of 1-(4-methoxyphenyl)-1-propanone

Anisole (540 μl, 4.9 mmol) and propionic acid anhydride (130 μl, 1 mmol) were added to 1-ethyl-3-methylimidazolium trifluoromethanesulfonate (1.5715 g, 6 mmol), previously dried during 2 h at 80° C. The mixture was heated to 80-85° C. in a hermetically closed vessel. After 2 h of standing, the crude product was extracted with diethyl ether, filtered through a silica column and concentrated under reduced pressure to give 121.2 mg of the title compound. Yield: 65.5% (calculated by gas chromatography (GC) with internal standard). Selectivity orto/para: 0/100.

Example 2

Preparation of 1-(4-methoxyphenyl)-1-butanone

Anisole (540 μl, 4.9 mmol) and butanoic acid anhydride (160 μl, 0.98 mmol) were mixed with 1-ethyl-3-methylimidazolium trifluoromethanesulfonate (1.5139 g, 5.82 mmol) at 80° C. during 2 h as in Example 1. The work-up was also analogous to the one described in Example 1 to give 114.0 mg of the title compound. Yield: 57% (calculated by GC with internal standard). Selectivity orto/para: 0/100.

Example 3

Preparation of (4-methoxyphenyl)phenylmethanone

Anisole (540 μl, 4.9 mmol) and benzoic acid anhydride (0.2304 g, 1.02 mmol) were mixed with 1-ethyl-3-methylimidazolium trifluoromethanesulfonate (1.5420 g, 5.92 mmol) at 80° C. during 2 h, analogously to the previous examples. After the work-up 192.2 mg of the title compound were obtained. Yield: 52% (calculated by GC with internal standard). Selectivity orto/para: 0/100.

Example 4

Preparation of (4-methoxyphenyl)phenylmethanone

Anisole (540 μl, 4.9 mmol) and benzoic acid anhydride (0.2733 g, 1.21 mmol) were mixed with 1,3-diethylimidazolium trifluoromethanesulfonate (1.4634 g, 5.34 mmol) at 80° C. during 2 h as in the previous examples. After the work-up 253.4 mg of the title compound were obtained. Yield: 34% (calculated by GC with internal standard). Selectivity orto/para: 0/100.

The invention claimed is:

1. A process for preparation of aromatic ketones by a Friedel-Crafts acylation reaction in an ionic liquid, between a Friedel-Crafts aromatic substrate and a Friedel-Crafts acylating agent, wherein the ionic liquid has the formula (I) and is used in the absence of any other catalyst and/or solvent; wherein [Q]$^+$ is selected from the group consisting of a substituted-imidazolium cation, a substituted-pyridinium cation, an ammonium cation, and a phosponium cation.

$$[Q]^+[CF_3SO_3]^- \qquad (I)$$

2. The process according to claim 1, wherein [Q]$^+$ is a substituted-imidazolium cation.

3. The process according to claim 2, wherein the ionic liquid is selected from the group consisting of 1-ethyl-3-methylimidazolium trifluoromethanesulfonate, 1,3-diethylimidazolium trifluoromethanesulfonate, and 1,3-dimethylimidazolium trifluoromethanesulfonate.

4. The process according to claim 3, wherein the ionic liquid is 1-ethyl-3-methylimidazolium trifluoromethanesulfonate.

5. The process according to claim 1, wherein the Friedel-Crafts acylating agent is selected from the group consisting of a carboxylic acid halide, a carboxylic acid anhydride, a carboxylic acid ester and a carboxylic acid.

6. The process according to claim 5, wherein the Friedel-Crafts acylating agent is a carboxylic acid anhydride.

7. The process according to claims 5, wherein the acylating agent is selected from the group consisting of acetic acid anhydride, propionoic acid anhydride, butanoic acid anhydride, isobutanoic acid anhydride, pentanoic acid anhydride, benzoic acid anhydride, chloroacetic acid anhydride, acetyl chloride, propanoyl chloride, butanoyl chloride, benzoyl chloride, and chloroacetyl chloride.

8. The process according to claim 1, wherein the Friedel-Crafts aromatic substrate is selected from the group consisting of aromatic benzenoid compounds, aromatic benzenoid-fused compounds, and heteroaromatic compounds resulting from substitution of CH groups by N atoms in said aromatic benzenoid compounds and aromatic benezenoid-fused compounds; said aromatic and heteroaromatic substrates being optionally substituted by substituents which are stable under Friedel-Crafts reaction conditions, or which have been suitably protected to be stable.

9. The process according to claim 8, wherein the Friedel-Crafts aromatic substrate is selected from the group consisting of benzene, toluene and anisole.

10. The process according to claim 9, wherein the Friedel-Crafts aromatic substrate is anisole.

11. The process according to claim 1, wherein the Friedel-Crafts acylating agent is attached to the Friedel-Crafts aromatic substrate, the carbonyl group of the Friedel-Crafts acylating agent being separated from the Friedel-Crafts aromatic substrate by a aliphatic chain from 2 to 4 carbon atoms, effecting an intramolecular ring closure and yielding a (5-7)-membered ring.

12. The process according to any one of claims 1-6 and 8-9, wherein the reaction is carried out at a temperature between room temperature and 150° C.

13. The process according to any one of claims 1-6 and 8-9, wherein the reaction is carried out at a temperature between 70° C. and 100° C.

14. The process according to claim 6, wherein the acylating agent is selected from the group consisting of acetic acid anhydride, propionoic acid anhydride, butanoic acid anhydride, isobutanoic acid anhydride, pentanoic anhydride, benzoic acid anhydride, chloroacetic acid anhydride, acetyl chloride, propanoyl chloride, butanoyl chloride, benzoyl chloride, and chloroacetyl chloride.

15. The process according to claim 1, wherein the ionic liquid is used in the absence of any other catalyst and solvent.

16. The process according to claim 14, wherein the reaction is carried out at a temperature between room temperature and 150° C.

* * * * *